(12) United States Patent
Solomon et al.

(10) Patent No.: US 9,414,470 B2
(45) Date of Patent: Aug. 9, 2016

(54) HAND HELD SKIN TREATMENT DEVICE

(75) Inventors: Philip Solomon, Kibbutz Tzora (IL);
Dolev Rafaeli, Cresskill, NJ (US)

(73) Assignee: RADIANCY INC., Orangeburg, NY (US)

( * ) Notice: Subject to any disclaimer, the term of this patent is extended or adjusted under 35 U.S.C. 154(b) by 1637 days.

(21) Appl. No.: 12/738,842

(22) PCT Filed: Oct. 5, 2008

(86) PCT No.: PCT/IL2008/001319
§ 371 (c)(1),
(2), (4) Date: Apr. 20, 2010

(87) PCT Pub. No.: WO2009/053965
PCT Pub. Date: Apr. 30, 2009

(65) Prior Publication Data
US 2010/0241110 A1  Sep. 23, 2010

Related U.S. Application Data

(60) Provisional application No. 60/981,820, filed on Oct. 22, 2007.

(51) Int. Cl.
*A61N 5/06* (2006.01)
*H05B 39/04* (2006.01)
*A61B 18/20* (2006.01)
(Continued)

(52) U.S. Cl.
CPC ............ *H05B 39/044* (2013.01); *A61B 18/203* (2013.01); *A61B 2017/00084* (2013.01); *A61B 2017/00172* (2013.01); *A61B 2018/0047* (2013.01); *A61B 2018/00452* (2013.01); *A61B 2018/1807* (2013.01); *A61N 5/0616* (2013.01);
(Continued)

(58) Field of Classification Search
None
See application file for complete search history.

(56) References Cited

U.S. PATENT DOCUMENTS 4,902,958 A    2/1990  Cook, II
6,214,034 B1 *  4/2001  Azar ............................. 607/90
(Continued)

FOREIGN PATENT DOCUMENTS

JP    S64-397592    3/1989

OTHER PUBLICATIONS

Response to Office action for parallel European Application 08 841 777.9-2305 of mailing date Mar. 31, 2011 filed at European Patent Office on Jul. 7, 2011.
(Continued)

*Primary Examiner* — Jessica Stultz
*Assistant Examiner* — Sean Hagan
(74) *Attorney, Agent, or Firm* — Simon Kahn; Chanoch Kahn

(57) ABSTRACT

A hand held, home use, device for treatment of skin, comprising: a housing exhibiting an opening therein and forming an air cavity when the opening is placed in contact with the skin; an incandescent type bulb secured within the housing and arranged to irradiate the skin with infra-red radiation and heat air within the formed air cavity, the incandescent type bulb exhibiting a filament; and a control and driving circuitry in electrical communication with the incandescent type bulb and operative to output a train of pulses exhibiting an on time when current is driven through the filament and an off time when current is not driven through the filament, the off time greater than or equal to the on time, the off time being of a duration such that the infra-red radiation irradiating the skin falls, during the off time, to no less than 25% of its maximum value.

29 Claims, 4 Drawing Sheets

(51) Int. Cl.
*A61B 17/00* (2006.01)
*A61B 18/00* (2006.01)
*A61B 18/18* (2006.01)

(52) U.S. Cl.
CPC . *A61N 2005/0644* (2013.01); *A61N 2005/0659* (2013.01); *Y02B 20/146* (2013.01)

(56) References Cited

U.S. PATENT DOCUMENTS

| | | | |
|---|---|---|---|
| 6,409,744 | B1 | 6/2002 | Marchesi |
| 6,605,080 | B1 * | 8/2003 | Altshuler et al. ............... 606/13 |
| 2001/0001818 | A1 | 5/2001 | Hibst |
| 2003/0236487 | A1 | 12/2003 | Knowlton |
| 2005/0045189 | A1 | 3/2005 | Jay |
| 2006/0052847 | A1 | 3/2006 | Davenport |
| 2006/0206103 | A1 * | 9/2006 | Altshuler et al. ................. 606/9 |
| 2007/0194725 | A1 | 8/2007 | Johnson |
| 2007/0213792 | A1 | 9/2007 | Yaroslavsky |

OTHER PUBLICATIONS

International Search Report for PCT/IL2008/001319 by European Patent Office mailed Feb. 20, 2009.
Written Opinion of the International Searching Authority for PCT/IL2008/001319 by European Patent Office mailed Feb. 20, 2009.
Communication from European Patent Office Dated Mar. 31, 2011 regarding European parallel application 08 841 777.9-2305.
Japanese Patent Office Rejection dated May 7, 2013, for parallel patent application JP 2010-530626.

* cited by examiner

HAND HELD SKIN TREATMENT DEVICE

BACKGROUND

The invention relates generally to the field of dermatological devices and in particular to a hand held device exhibiting rapid pulsing of an incandescent light source to exhibit low intensity light therapy without requiring skin cooling.

Electromagnetic energy, and particularly light energy in the visible and near infra-red ranges are widely used in medical applications to treat skin disorders. Localized heating is also widely used to treat skin disorders; however the temperature of the skin must be carefully monitored to prevent overheating with resulting damages. A large range of medical skin conditions, and general aesthetic skin conditions are successfully treated with electromagnetic energy, including but not limited to acne, wrinkle eradication, skin tightening and skin rejuvenation, as well as acne.

While a wide range of electromagnetic radiation has been used to treat various conditions, it is important to note that infra-red radiation, particularly infra-red radiation about the 1450 nm range, is most successful in penetrating the dermis and being absorbed by water molecules. Light in the infra-red range thus causes soft tissue coagulation which leads to remodeling of the collagen within the dermis. The remodeled collagen fills in wrinkles and sagging, resulting in overall skin tightening.

A combination of light and heat energy is known to be effective in clearing acne. The LHE® line of products from Radiancy Inc. of Orangeburg, N.Y. is known to clear acne safely and effectively with a series of concentrated pulses of light and heat. The green wavelength light penetrates deep into the skin to cause an increase in porphyrins, resulting in the destruction of Propionibacterium. The red wavelength produces anti-inflammatory results. The addition of heat increases the effectiveness by opening the skin pores and promoting a faster chemical reaction. It is believed that the infra-red portion of the light, which is successful in penetrating the dermis, is most effective.

Such a combination of light and heat energy, in which a pulsed radiant heat source, such as a laser beam of substantially monochromatic radiant energy, a flash lamp, a xenon arc lamp or a quartz flash lamp, is taught in U.S. Patent Application Publication S/N 2004/0167498 A1 published Aug. 26, 2004 to Azar et al, the entire contents of which are incorporated herein by reference. Unfortunately the use of laser beams, flash lamps, xenon arc lamps or quartz flash lamps increase the size and cost of the device, and are not appropriate for home use, where a small handheld device is preferred not requiring supervision by trained personnel.

There is thus a long felt need for a hand held, home use, device exhibiting heat and light for the treatment of skin.

SUMMARY

Accordingly, it is a principal object to overcome at least some of the disadvantages of prior art devices for skin treatment. This is accomplished in certain embodiments by a hand held, home use, device exhibiting an incandescent type bulb driven by a train of pulses exhibiting a low duty cycle, defined as the percentage on time, of preferably less than or equal to 50%, further preferably less than or equal to 33%, even further preferably less than or equal to 25%. The incandescent type bulb is arranged within an air cavity, and placed at one end thereof, and the target skin is placed at the opposite end of the air cavity. Thus, the pulsing of the incandescent type bulb impacts the skin with light by radiation; and heat by conduction and/or convection. The incandescent type bulb, preferably a halogen type bulb, is provided without a filter, thereby producing a combination of infra-red and visible light.

The duty cycle is arranged such that during the off time the infra-red radiation decreases, however a continuous flux of infra-red radiation is maintained by controlling the off time. Preferably, the flux of infra-red radiation falls to no less than 25% of its maximum value during its off time. Thus, a continuous flux of infra-red radiation is maintained while pulsing the bulb so as to prevent the production of excess heat.

In some embodiments the on time of each of the pulses less than 150 milliseconds. In another embodiment the incandescent type bulb exhibits a nominal color temperature output of about 2000° Kelvin, preferably 2000°-2300° K. In yet other embodiments the incandescent type bulb exhibits a nominal luminous output of 200-800 lumens, preferably 250-400 lumens.

In some embodiments the pulsed light output exhibits an average power per pulse of no more than 2 Watts/cm$^2$ when measured at said skin and averaged over the on time and the off time, and preferably no more than 0.6 Watts/cm$^2$ when so measured. In other embodiments the train of pulses is maintained for a period of 5-45 seconds, preferably 5-25 seconds, thereby defining a treatment, the treatment exhibiting no more than 25 Joules/cm$^2$ when measured at said skin, preferably no more than 8 Joules/cm$^2$ when so measured.

In some embodiments a temperature sensor is further provided, the device being operative responsive to an output of the temperature sensor to increase the off time of the train of pulses in the event that the sensed temperature exceeds a predetermined value.

Additional features and advantages will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PREFERRED EMBODIMENTS

Figure 1:
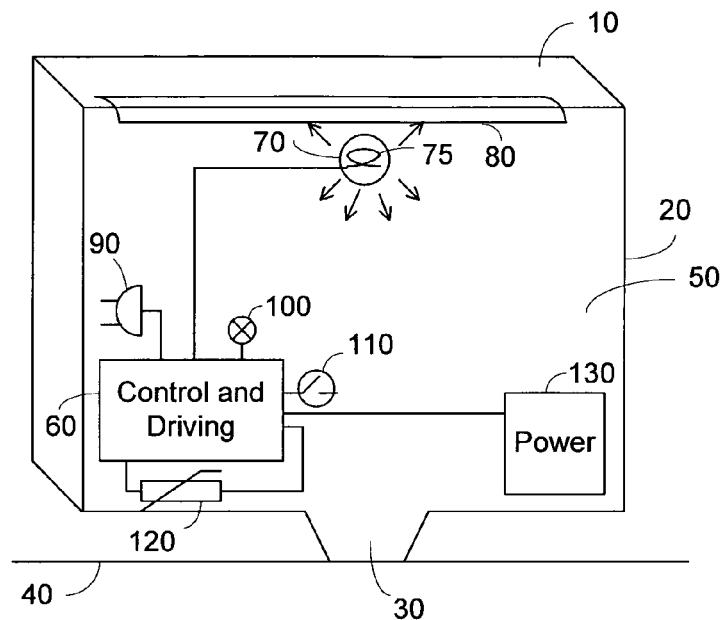
FIG. 1 illustrates a high level block diagram of a hand held device in accordance with certain embodiments.

Certain of the present embodiments enable a hand held, home use, device exhibiting an incandescent type bulb driven by a train of pulses exhibiting a low duty cycle of less than or equal to 50%, preferably less than or equal to 33%, further preferably less than or equal to 25%. The incandescent type bulb is arranged within an air cavity, and placed at one end thereof, and the target skin is placed at the opposite end of the air cavity. Thus, the pulsing of the incandescent type bulb impacts the skin with light by radiation; and heat by conduction and/or convection. The incandescent type bulb, preferably a halogen type bulb, is provided without a filter, thereby producing a combination of infra-red and visible light.

The duty cycle is arranged such that during the off time the infra-red radiation decreases, however a continuous flux of infra-red radiation is maintained by controlling the off time. Preferably, the flux of infra-red radiation falls to no less than 25% of its maximum value during its off time. Thus, a continuous flux of infra-red radiation is maintained while pulsing the bulb so as to prevent the production of excess heat.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1 illustrates a high level block diagram of a hand held device 10 in accordance with certain embodiments comprising: a housing 20 exhibiting an opening 30 arranged for placement in contact with a user skin 40 and forming an air cavity 50; a control and driving circuitry 60; an incandescent type bulb 70 comprising a filament 75; a reflector 80; an audible alarm 90; a visual indicator 100; a user input 110; a temperature sensor 120; and a rechargeable power source 130.

User input 110, preferably a push button, is arranged to receive a user input, and is in communication with control and driving circuitry 60. Visual indicator 100, which preferably comprises one or more LEDs or an LCD display, is operative to provide the user with a status indication, such as a charging status of rechargeable power source 130, operation of incandescent type bulb 70 and/or temperature range of the skin responsive to the output of temperature sensor 120. Visual indicator 100 is in communication with control and driving circuitry 60. Temperature sensor 120 is arranged to sense a temperature associated with the temperature of the skin located opposite opening 30, and is in communication with control and driving circuitry 60. Audible alarm 90, which in one embodiment is constituted of a buzzer, is operative to audibly notify a user of the operation of incandescent type bulb 70, and is driven by an output of control and driving circuitry 60.

Incandescent type bulb 70 is secured within housing 20 and receives pulsed power from control and driving circuitry 60 exhibiting an on time during which a current is driven through filament 75 and an off time during which current is not driven through filament 75. It is to be understood that a minimal amount of current may be passed through during the off time, however the current is insufficient to produce infra-red energy. Incandescent type bulb 70 is arranged to irradiate user skin 40 with infra-red and visible light and to heat air within air cavity 50 when pulsed by control and driving circuitry 60. The heated air of air cavity 50 further heats user skin 40 via a temperature gradient formed between incandescent type bulb 70 and opening 30. Reflector 80 is disposed within housing 20 and is arranged to reflect light exiting incandescent bulb 70 towards opening 30.

The term visible light, as used herein, is meant to include wavelengths of 500-900 nm. The term infra-red light or energy, as used herein, is meant to include wavelengths of above 900 nm up to about 1700 nm.

Control and driving circuitry 60 is connected to rechargeable power source 130, and is operative to monitor the status thereof, control charging thereof and draw power there from.

Figure 2:
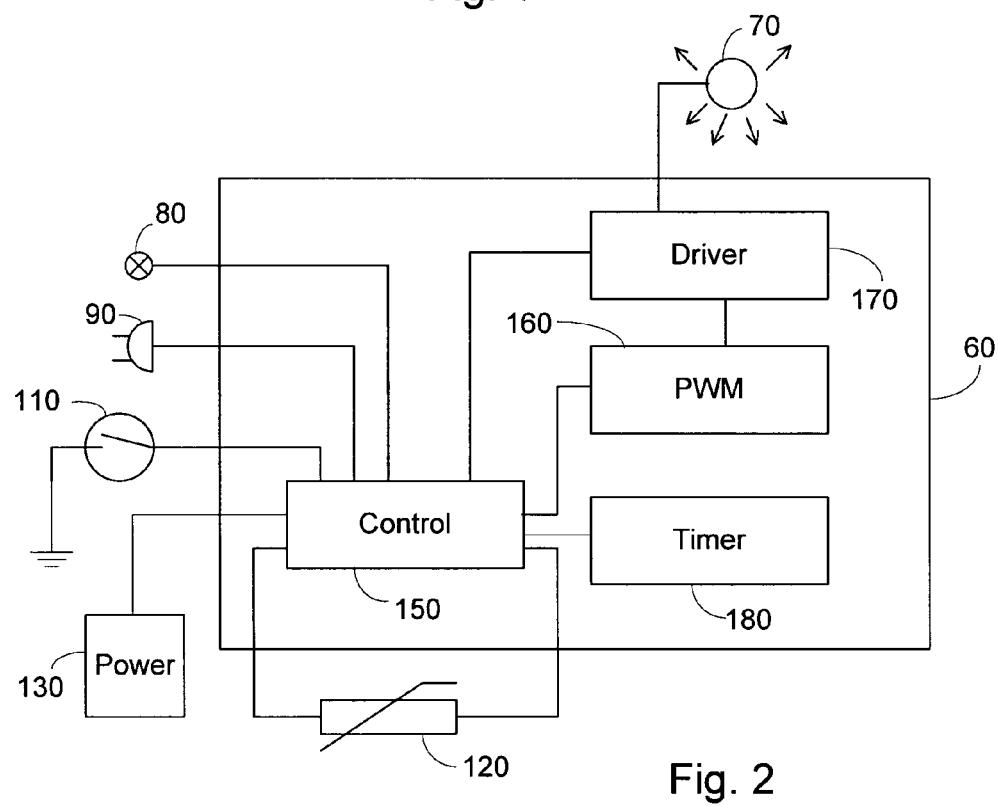
FIG. 2 illustrates a high level schematic diagram of the circuitry of the hand held device of FIG. 1 in accordance with certain embodiments.

FIG. 2 illustrates a high level schematic diagram of the circuitry of hand held device 10 of FIG. 1 in accordance with certain embodiments, in which the pulse train is generated by a pulse width modulation generator. Control and driving circuitry 60 comprises a control block 150, a pulse width modulation (PWM) generator 160, a driving circuitry 170 and a timer 180. Control block 150 is in communication with PWM generator 160, driving circuitry 170 and timer 180. The output of PWM generator 160 is fed to driving circuitry 170, and the output of driving circuitry 170 is connected to incandescent type bulb 70. A port of control block 150 is connected to sense a user action at user input 110, and a port of control block 150 is connected to each of audible alarm 90 and visual indicator 100. Temperature sensor 120 is in communication with control block 150, and rechargeable power source 130 is in communication with control block 150.

In operation, control block 150 monitors the status of rechargeable power source 130. In the event that rechargeable power source 130 is connected to an external charging source, and the voltage of rechargeable power source 130 exceeds a predetermined maximum, charging of rechargeable power source is interrupted.

Responsive to a user action at user input 110, control block 150 is activated to begin a treatment session. Visual indicator 100 is set to indicate operation, and PWM generator 160 is enabled, to produce a pulse train exhibiting less than or equal to a 50% duty cycle, preferably less than or equal to a 33% duty cycle, further preferably less than or equal to up to a 25% duty cycle. The precise duty cycle is a function of actual incandescent type bulb 70, and the driving current. Preferably, the duty cycle is selected such that during the off time of the cycle, the infra-red radiation does not fall to less than 25% of the maximum value. The maximum value is defined during the on time of the cycle, preferably at the end of the on time of the cycle. Once PWM generator 160 is stabilized driving circuitry 170 is enabled, thereby driving incandescent type bulb 70 with a pulse train, and timer 180 is initialized.

Driving circuitry 170 preferably comprises current sensing circuitry, enabling control of the current driving incandescent type bulb 70. The current of driving circuitry 170 is in one embodiment selected so as to result in an average energy of no more than 2 Watts/cm$^2$ measured opposite opening 30. In another embodiment the current of driving circuitry 170 is in one embodiment selected so as to result in an average energy of no more than 0.6 Watts/cm$^2$ measured opposite opening 30. Preferably, the current and rating of incandescent type bulb 70 results in a nominal luminous output, measured opposite opening 30, of about 200-800 lumens, further preferably 250-400 lumens.

In order to maximize the portion of energy in the infra-red range, without the added expense of filters, an incandescent bulb exhibiting a nominal color temperature of about 2000° K., preferably 2000°-2300° K. is preferred. Pulsing the filament with a low duty cycle, results in a further improvement in the ratio of infra-red light to visible light.

Control block 150 monitors temperature sensor 120, and in the event temperature sensor 120 indicates a temperature in excess of a predetermined maximum, control block 150 reduces the duty cycle output by PWM generator 160 thereby reducing the overall energy and heat generated. In the event that temperature sensor 120 indicates a temperature in excess of a predetermined higher cut-off maximum, control block 150 disables driving circuitry 170 so as to prevent burn of user skin 40. Control block 150 further monitors the time elapsed since enabling driving circuitry 170 via timer 180, and after the expiration of timer 180, set with a predetermined treatment time, control block 150 disables driving circuitry 170. In a preferred embodiment, audible alarm 90 is sounded at the end of the predetermined treatment time, or in the event of a temperature in excess of the predetermined maximum.

Figure 3:
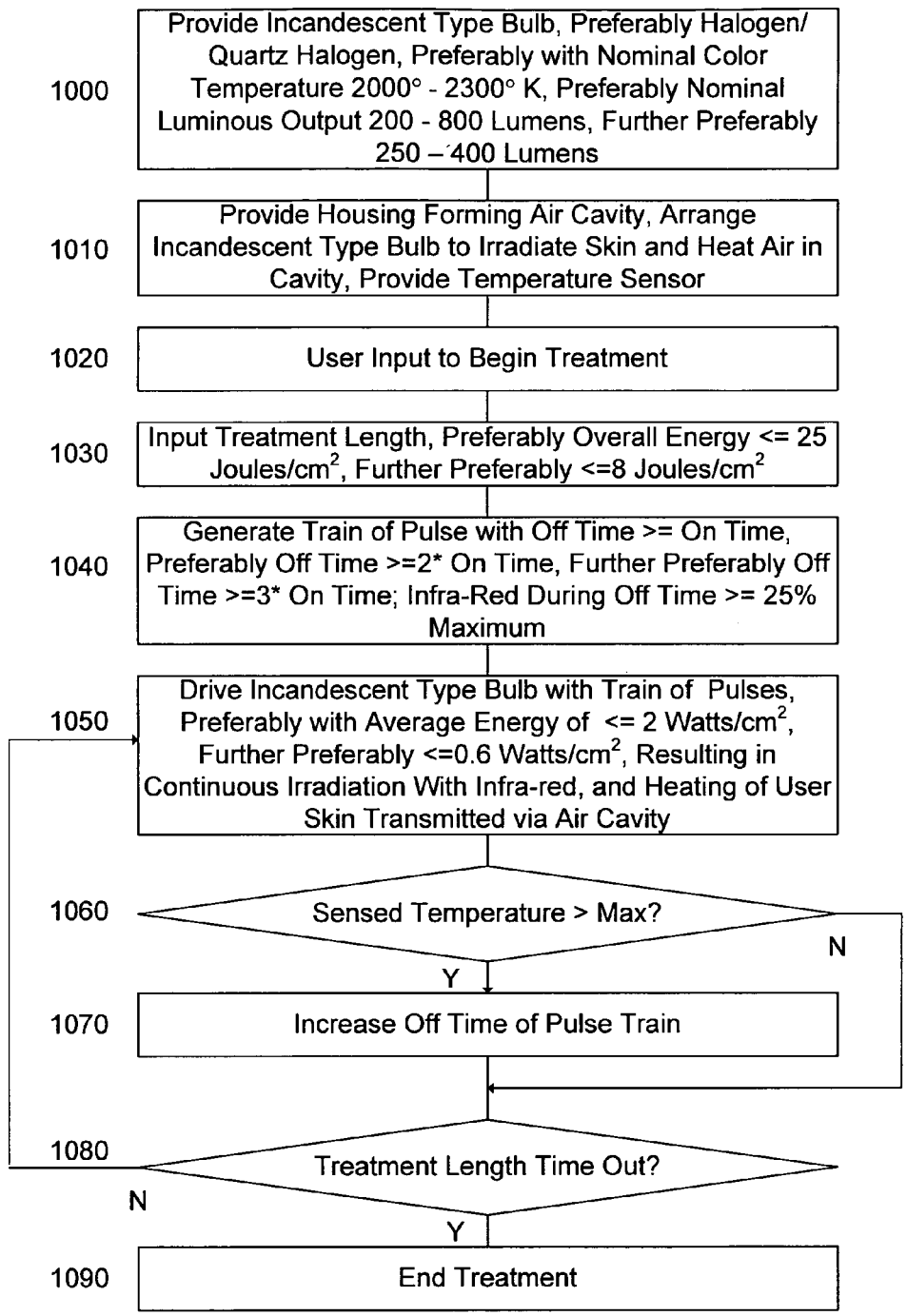
FIG. 3 illustrates a high level flow chart of the operation and preparation of the hand held device of FIG. 1 in accordance with certain embodiments.

FIG. 3 illustrates a high level flow chart of the operation and preparation of hand held device 10 in accordance with certain embodiments. In stage 1000, an incandescent type bulb, such as incandescent type bulb 70, preferably a halogen bulb, more preferably a quartz halogen bulb is provided, the incandescent bulb comprising a filament. Preferably, the incandescent type bulb exhibits a nominal color temperature output of about 2000° K., preferably 2000°-2300° K. Preferably, the incandescent type bulb exhibits a nominal luminous output of 200-800 lumens, further preferably 250-400 lumens.

In stage 1010, a housing is provided, such as housing 20, the housing forming an air cavity with an opening arranged to be in contact with, or in close proximity to, the area of skin to be treated. The incandescent type bulb of stage 1000 is arranged within the provided housing so as to irradiate skin via the opening, such as opening 30. Optionally a reflector is further provided to reflect an increased amount of light exiting the incandescent type bulb towards the opening. The incandescent type bulb is further arranged to heat air in the cavity, thereby producing a heat gradient between the incandescent type bulb and the skin and heating the skin opposing opening 30 by conduction and/or convection. Optionally, a temperature sensor, such as temperature sensor 120, is provided and arranged to sense the temperature associated with a target skin.

In stage 1020, a user action is sensed, such as by user input 110, indicating a desire for treatment. In stage 1030, a treatment length is input. In one embodiment, the treatment length is a fixed time stored in a memory on control block 150. In another embodiment, the treatment length is user selectable via user input 110. The treatment length is preferably stored in a timer, such as timer 180. Preferably, the treatment length is controlled such that the overall fluence delivered to the skin is less than or equal to 25 Joules/cm$^2$, further preferably less than or equal to 8 Joules/cm$^2$.

In stage 1040, a train of pulses is generated exhibiting an off time greater than or equal to the on time, preferably an off time greater than or equal to twice the on time, and further preferably an off time greater than or equal to thrice the on time. In the event that the pulses are generated by a PWM generator, such as PWM generator 160, the pulses exhibit a duty cycle of less than or equal to 50%, preferably less than or equal to 33.3%, and further preferably less than or equal to 25%. The precise duty cycle is a function of actual incandescent type bulb, and the driving current, however is selected such that the infra-red radiation reaching the skin at opening 30 does not fall below 25% of the maximum value during the off time.

In stage 1050, the incandescent type bulb of stage 1000 is pulsed with a train of pulses of stage 1040. The driving current is preferably selected such that the average energy over a single on time and off time is less than or equal to 2 Watts/cm$^2$, preferably less than or equal to 0.6 Watts/cm$^2$, when measured at skin 40 placed opposite opening 30. The train of pulses results in a pulsed light output, comprising infra-red and visible radiation, and further heats air in the air cavity for transmission to the user skin via conduction and/or convection. Since the pulsing is controlled such that the fluence of infra-red is continuous, the electromagnetic energy is advantageously tilted towards the infra-red without requiring expensive filters. The heated air advantageously acts to further open and dry skin pores.

In stage 1060, the output of the temperature sensor of stage 1010 is compared with a maximum temperature indication. In the event that the temperature indicated by the temperature sensor exceeds the predetermined maximum, in stage 1070, the temperature is reduced by increasing the off time of the pulse train. It is to be understood that preferably a second higher cut off maximum temperature is further provided, and in the event the second higher cut off maximum temperature is exceeded, treatment is stopped by disabling the driving circuitry, such as driving circuitry 170. Optionally, when either the maximum temperature and/or the higher cut off maximum temperature is exceeded, an audible alarm indication is given to the user via audible alarm 90. Optionally, a visual indication is given to the user via visual indicator 100.

In stage 1080 the running treatment length time of stage 1030 is checked. In the event that the treatment length time has expired, in stage 1090 treatment is terminated. Optionally one or more of an audible alarm user via audible alarm 90 and a visual indication is given via visual indicator 100 is provided at treatment termination.

In the event that in stage 1080 the treatment length time has not expired, stage 1050 as described above, is performed. In the event that in stage 1060 the temperature indicated by the temperature sensor does not exceed the predetermined maximum, stage 1080 as described above is performed.

The operation of stage 1080 has been described as checking a timer, however this is not meant to be limiting in any way. In another embodiment, stage 1080 is initiated by an interrupt caused by the expiration of timer 180.

Figure 4A:
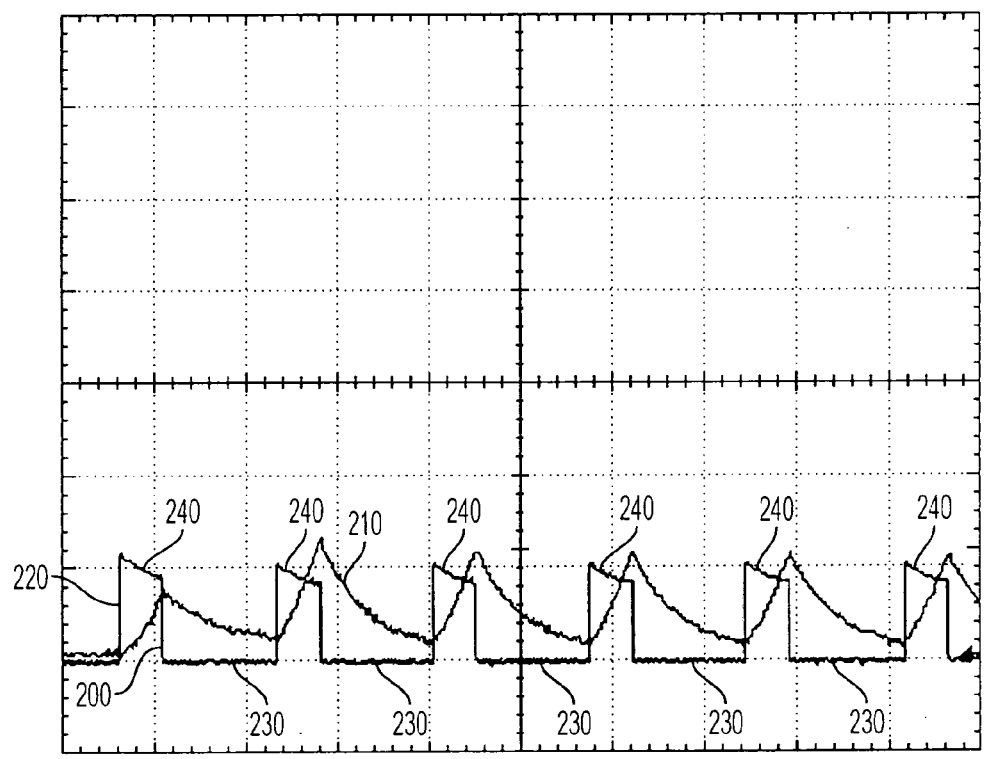
FIG. 4A illustrates a graph of an embodiment of the pulse train driving the incandescent type bulb of the hand held device of FIG. 1, and the visible light output resulting thereof, in accordance with in accordance with certain embodiments.

FIG. 4A illustrates a graph of an embodiment of the pulse train driving filament 75 of the incandescent type bulb 70 of hand held device 10 of FIG. 1 in accordance with certain embodiments, in which the current of the pulse train is denoted curve 200, and the visible light output is denoted curve 210, and in which the x-axis represents time and the y-axis represents amplitude. Curve 200 exhibits a leading pulse 220, exhibiting a maximum amplitude, reflective of the cold state and resultant low resistance of the filament at start up. The amplitude of pulse 220 declines over time, responsive to the heating of the filament. Visible light output, as shown by curve 210, begins responsive to the leading edge of leading pulse 220, with a small delay. Curve 200 further exhibits a plurality of repetitive pulses exhibiting an off time 230 and an on time 240. Off time 230 is at least equal to on time 240, preferably off time 230 is at least twice on time 240, further preferably off time 230 is at least three time on time 240. Visible light curve 210 rises responsive to the on time 240 and falls to a near negligible amplitude at the end of each off time 230.

Figure 4B:
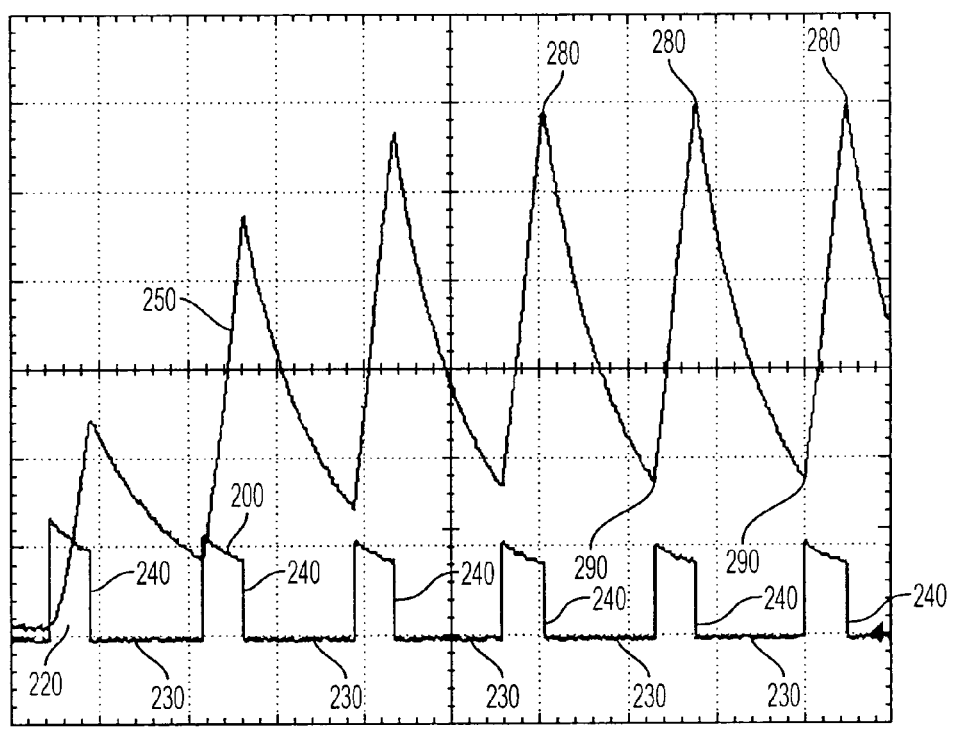
FIG. 4B illustrates a graph of an embodiment of the pulse train driving the incandescent type bulb of the hand held device of FIG. 1, and the infra-red light output resulting thereof, in accordance with certain embodiments.

FIG. 4B illustrates an embodiment of the pulse train driving filament 75 of the incandescent type bulb 70 of hand held device 10 of FIG. 1 in accordance with certain embodiments, in which the current of pulse train is denoted curve 200, and the infra-red light output is denoted curve 250, and in which the x-axis represents time and the y-axis represents amplitude. Curve 200 exhibits a leading pulse 220, exhibiting a maximum amplitude, reflective of the cold state and resultant low resistance of the filament at start up. The amplitude of leading pulse 220 declines over time, responsive to the heating of the filament. Infra-red light output, as shown by curve 250, begins responsive to the leading edge of leading pulse 220, with a small delay. Curve 200 further exhibits a plurality of repetitive pulses exhibiting an off time 230 and an on time 240. Off time 240 is at least twice on time 230. Infra-red light curve 250 rises responsive to the on time 240 and falls during each off time 230.

The peak amplitude of infra-red light curve 250 reaches a steady state, as shown by peak 280 after a plurality of on time 230 cycles. Infra-red light curve 250 declines during each off time 230 to a minimum value 290. Minimum value 290 is non-negligible, and is no less than 25% of peak value 280.

Thus, certain of the present embodiments enable a hand held, home use, device exhibiting an incandescent type bulb driven by a train of pulses exhibiting a low duty cycle, preferably less than or equal to 50%, further preferably less than or equal to 33%, even further preferably less than or equal to 25%. The incandescent type bulb is arranged within an air cavity, and placed at one end thereof, and the target skin is placed at the opposite end of the air cavity. Thus, the pulsing of the incandescent type bulb impacts the skin with light by radiation; and heat by conduction and/or convection. The incandescent type bulb, preferably a halogen type bulb, is provided without a filter, thereby producing a combination of infra-red and visible light.

The duty cycle is arranged such that during the off time the infra-red radiation decreases, however a continuous flux of infra-red radiation is maintained by controlling the off time. Preferably, the flux of infra-red radiation falls to no less than 25% of its maximum value during its off time. Thus, a continuous flux of infra-red radiation is maintained while pulsing the bulb so as to prevent the production of excess heat.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. In the claims of this application and in the description of the invention, except where the context requires otherwise due to express language or necessary implication, the word "comprise" or variations such as "comprises" or "comprising" is used in any inclusive sense, i.e. to specify the presence of the stated features but not to preclude the presence or addition of further features in various embodiments of the invention.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting. No admission is made that any reference constitutes prior art. The discussion of the reference states what their author's assert, and the applicants reserve the right to challenge the accuracy and pertinency of the cited documents. It will be clearly understood that, although a number of prior art complications are referred to herein, this reference does not constitute an admission that any of these documents forms part of the common general knowledge in the art in any country.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

We claim:

1. A hand held device for treatment of skin, the device comprising:
   a housing exhibiting an opening therein and forming an air cavity enclosing a volume of air when said opening is placed in contact with the skin;
   an incandescent type bulb exhibiting a filament, said incandescent bulb secured within said housing and arranged to output heat, visible light and infrared radiation responsive to current flow through said filament, said housing arranged to:
   allow said infrared radiation output by said incandescent type bulb to irradiate the skin; and
   heat air within said formed air cavity responsive to the heat output by said incandescent type bulb, wherein the heated air within said formed air cavity forms a temperature gradient between said incandescent type bulb and the skin via said opening thereby heating the skin; and
   a control and driving circuitry in electrical communication with said incandescent type bulb and operative to output a train of pulses exhibiting an on time when current is driven through said filament and an off time when current is not driven through said filament, said off time greater than or equal to said on time, said off time of a duration such that said infra-red radiation irradiating the skin falls, during said off time, to no less than 25% of its maximum value, and wherein the visible light output of said incandescent type bulb falls to a near zero value during said off time.

2. A hand held device according to claim 1, wherein said off time is greater than or equal to twice said on time.

3. A hand held device according to claim 1, wherein said off time is greater than or equal to thrice said on time.

4. A hand held device according to claim 1, wherein said on time is less than 150 milliseconds.

5. A hand held device according to claim 1, wherein said incandescent type bulb exhibits a nominal color temperature output of about 2000° Kelvin.

6. A hand held device according to claim 1, wherein said incandescent type bulb exhibits a nominal color temperature output of about 2000°-2300° Kelvin.

7. A hand held device according to claim 1, wherein said incandescent type bulb exhibits a nominal luminous output of 200-800 lumens.

8. A hand held device according to claim 1, wherein said incandescent type bulb exhibits a nominal luminous output of 250-400 lumens.

9. A hand held device according to claim 1, wherein said incandescent type bulb is a halogen bulb.

10. A hand held device according to claim 1, wherein said pulsed light output exhibits an average energy per pulse of no more than 2 Watts/cm² when measured at said skin and averaged over a single one of said on time and said off time.

11. A hand held device according to claim 1, wherein said pulsed light output exhibits an average energy per pulse of no more than 0.6 Watts/cm² when measured at said skin and averaged over a single one of said on time and said off time.

12. A hand held device according to claim 1, wherein said control and driving circuitry maintains said train of pulses for a period of 5-45 seconds thereby defining a treatment, said treatment exhibiting no more than 25 Joules/cm² when measured at said skin.

13. A hand held device according to claim 1, wherein said control and driving circuitry maintains said train of pulses for a period of 5-25 seconds thereby defining a treatment, said treatment exhibiting no more than 8 Joules/cm² when measured at said skin.

14. A hand held device according to claim 1, further comprising a temperature sensor in communication with said control and driving circuitry, secured to said housing and arranged to sense a temperature associated with the skin,
said control and driving circuitry being further operative responsive to an output of said temperature sensor to increase said off time of said train of pulses in the event said sensed temperature exceeds a predetermined value.

15. A method of treating skin, said method comprising:
providing a housing exhibiting an opening therein and forming an air cavity enclosing a volume of air when said opening is placed in contact with the skin;
providing an incandescent type bulb comprising a filament and outputting visible light, heat and infra-red radiation responsive to current flow through the filament, said provided incandescent bulb secured within said provided housing and arranged to irradiate the skin with the output infra-red radiation and further arranged to heat air within said formed air cavity, wherein the heated air within said formed air cavity forms a temperature gradient between said incandescent type bulb and the skin via said opening thereby heating the skin; and
pulsing said provided incandescent type bulb with a train of pulses exhibiting an on time when current is driven through said filament and an off time when current is not driven through said filament, said off time greater than or equal to said on time, said off time being of a duration such that said infra-red radiation irradiating the skin falls, during said off time, to no less than 25% of its maximum value, and wherein the visible light output of said incandescent type bulb falls to a near zero value during said off time.

16. A method according to claim 15, wherein said off time is greater than or equal to twice said on time.

17. A method according to claim 15, wherein said off time is greater than or equal to thrice said on time.

18. A method according to claim 15, further comprising:
providing a housing exhibiting an opening therein and forming an air cavity enclosing a volume of air when said opening is placed in contact with the skin; and
arranging said provided incandescent type bulb within said housing so as to irradiate the skin with said infra-red radiation and heat air within said formed air cavity when pulsed.

19. A method according to claim 15, wherein said on time is less than 150 milliseconds.

20. A method according to claim 15, wherein said provided incandescent type bulb is a halogen bulb.

21. A method according to claim 15, wherein said provided incandescent type bulb exhibits a nominal color temperature output of about 2000° Kelvin.

22. A method according to claim 15, wherein said incandescent type bulb exhibits a nominal color temperature output of about 2000°-2300° Kelvin.

23. A method according to claim 15, wherein said provided incandescent type bulb exhibits a nominal luminous output of 200-800 lumens.

24. A method according to claim 15, wherein said provided incandescent type bulb exhibits a nominal luminous output of 250-400 lumens.

25. A method according to claim 15, wherein said provided, wherein said pulsed light output exhibits an average energy per pulse of no more than 2 Watts/cm² when measured at said skin and averaged over a single one of said on time and said off time.

26. A method according to claim 15, wherein said provided, wherein said pulsed light output exhibits an average energy per pulse of no more than 0.6 Watts/cm² when measured at said skin and averaged over a single one of said on time and said off time.

27. A method according to claim 15, wherein said train of pulses is maintained for a period of 5-45 seconds, defining a treatment.

28. A method according to claim 15, wherein said train of pulses is maintained for a period of 5-25 seconds, defining a treatment.

29. A method according to claim 15, further comprising:
sensing a temperature associated with the skin; and
increasing said off time of said train of pulses in the event said sensed temperature exceeds a predetermined value.

* * * * *